United States Patent [19]

Scheler

[11] Patent Number: 4,492,749
[45] Date of Patent: Jan. 8, 1985

[54] DIAZOTYPE MATERIALS WITH 2-HYDROXY-NAPHTHALENE HAVING SULFONAMIDE SUBSTITUENT AS COUPLER

[75] Inventor: Siegfried Scheler, Wiesbaden, Fed. Rep. of Germany

[73] Assignee: Hoechst Aktiengesellschaft, Frankfurt am Main, Fed. Rep. of Germany

[21] Appl. No.: 532,302

[22] Filed: Sep. 15, 1983

Related U.S. Application Data

[63] Continuation of Ser. No. 115,401, Jan. 25, 1980, abandoned.

[30] Foreign Application Priority Data

Jan. 29, 1979 [DE] Fed. Rep. of Germany ....... 2903342

[51] Int. Cl.³ .................................................. G03C 1/58
[52] U.S. Cl. .................................... 430/180; 430/148; 430/173; 430/176; 430/150; 430/8
[58] Field of Search ..................... 430/180, 148, 173

[56] References Cited

U.S. PATENT DOCUMENTS

| | | | |
|---|---|---|---|
| 2,298,444 | 10/1942 | Weissberger et al. | 430/180 |
| 2,537,098 | 1/1951 | Slifkin et al. | 430/181 |
| 2,551,570 | 5/1951 | Von Glahn et al. | 430/180 |
| 2,970,909 | 3/1961 | Slimowicz | 430/180 |
| 3,255,010 | 6/1966 | Sus et al. | 430/180 |
| 3,642,483 | 2/1972 | Kubo et al. | 430/180 |
| 3,645,741 | 2/1972 | Shiraishi et al. | 430/180 |
| 3,664,840 | 5/1972 | Saito et al. | 430/180 |
| 4,055,425 | 10/1977 | Mustacchi | 430/147 |
| 4,273,850 | 6/1981 | Frommeld | 430/180 |
| 4,334,004 | 6/1982 | Scheler | 430/180 |

OTHER PUBLICATIONS

Landau, R., "Fascicules 9 à 17", Andrews Paper & Chem. Co., Inc., pp. 19 and 69.

Primary Examiner—Charles L. Bowers, Jr.
Attorney, Agent, or Firm—Schwartz, Jeffery, Schwaab, Mack, Blumenthal & Koch

[57] ABSTRACT

This invention relates to a derivative of 2-hydroxy-naphthalene of the general formula

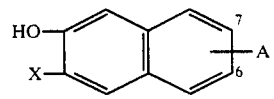

wherein A is

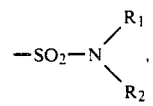

and X is —OH or

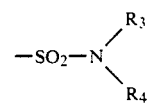

and $R_1$, $R_2$, $R_3$, and $R_4$ are identical or different and are hydrogen, cycloalkyl having up to eight carbon atoms, which is optionally substituted by lower alkyl groups, aralkyl having up to 10 carbon atoms or aryl which is substituted by lower alkyl, lower alkoxy, halogenalkyl or alkyl-substituted amino groups or by halogen, or $R_1$ and $R_2$ or $R_3$ and $R_4$ in each case are, conjointly with the nitrogen atom to which they are attached, identical or different heterocyclic groups which are optionally substituted by lower alkyl.

3 Claims, 1 Drawing Figure

DIAZOTYPE MATERIALS WITH 2-HYDROXY-NAPHTHALENE HAVING SULFONAMIDE SUBSTITUENT AS COUPLER

This is a continuation of application Ser. No. 115,401, filed 1-25-80, now abandoned.

This invention relates to derivatives of 2-hydroxynaphthalene, to the manufacture thereof and to the use thereof as coupling components in diazotype materials.

Compounds, such as 2,3-dihydroxy-naphthalene and the salts of 2,3-dihydroxy-naphthalene-6-sulfonic acid, 2-hydroxynaphthalene-3,6-disulfonic acid and 2-hydroxy-naphthalene-3,7-disulfonic acid, are known and they are employed, for example, as blue couplers in the diazotype process. In combination with components which couple to give yellow or brown colors, they also are used for diazotype materials which give black copies and which are particularly suitable as materials for intermediate originals for further duplicating.

A disadvantage of 2,3-dihydroxy-naphthalene is its high coupling activity which leads in unexposed diazotype materials to an undesirable premature coupling and hence to a low durability and storage stability. It is also disadvantageous that the diazo copy to be obtained from an original having different optical densities, a so-called "half-tone original", upon development gives different density values for different colors. On the other hand, the coupling of salts of 2,3-dihydroxy-naphthalene-6-sulfonic acid, 2-hydroxy-naphthalene-3,6-disulfonic acid and 2-hydroxy-naphthalene-3,7-disulfonic acid, among which particularly the sodium salts have gained importance, with the diazo compounds of the p-phenylenediamine type, which are customary in the diazotype process, is as a rule too slow. This disadvantage is particularly serious whenever a diazotype material which contains the slowly coupling components is to be developed at standard temperature with dry amounts gas under pressure. During the development with pressurized gas, favored because it does not pollute the environment, such diazotype materials develop only to give greenish-tinged grey color shades of very low contrast. It is also disadvantageous that the sodium salts of 2,3-dihydroxynaphthalene-6-sulfonic acid, 2-hydroxy-naphthalene-3,6-disulfonic acid and 2-hydroxy-naphthalene-3,7-disulfonic acid are virtually insoluble in organic solvents. They are thus unsuitable for a sensitization from an organic phase, such as is used in practice in the manufacture of transparent diazotype materials based on films.

The use of 2-hydroxy-3-naphthoic acid amides and of 2-hydroxy-3-naphthoic acid amides which are substituted in the 6-position by halogen or alkoxy (German Auslegeschrift No. 1,572,078 filed Apr. 27, 1966, which is equivalent to U.S. Pat. No. 3,493,377) as blue-coupling components in diazotype materials is also known. The disadvantage of these compounds is the undesirably high optical density of the image background in the long wavelength ultraviolet and short wavelength visible ranges of the spectrum. The most serious disadvantage of these blue couplers, however, is the inadequate light fastness of their azo dyes which are formed upon coupling with customary diazo compounds. A high light fastness of azo dyes, however, is desired whenever a copy, for example an engineering drawing, is exposed to sunlight for a prolonged period or a diazo intermediate original, which is used for the production of further diazo copies, is exposed to the actinic light of commercially available copying lamps.

The demands made with respect to the light fastness of diazotype azo dyes are very particularly high in the case of diazo microfilm copies. To evaluate their information content, such copies are exposed in readers and reader/magnifiers to a particularly intense radiation load-visible and ultraviolet light, and heat radiation- from the light sources built into these instruments. It frequently happens that diazo microfilm copies, which are exposed for a prolonged period to the emission of the incandescent lamps built into readers, fade to such an extent that the information stored thereon can then be read only with difficulty.

To improve the light fastness of diazotype azo dyes, 2-hydroxy-3-naphthoic acid amides with a sulfonamide group in the 6-position have also been proposed in the past (German patent application No. P 28 11 981.5, filed Mar. 18, 1978, which is equivalent to U.S. patent application Ser. No. 021,104, filed Mar. 16, 1979). These compounds couple with the diazo compounds, customary in the diazotype process, to give blue azo dyes of good light fastness. However, the coupling rate of these compounds, in particular during pressurized gas development and during conventional development with moist ammonia gas at low temperatures, is not always completely satisfactory for practical purposes.

The Landau Report, "Kupplungskomponenten (Coupling Components)", No. 9–17, 1962, discloses 2,3-dihydroxy-naphthalene-6-sulfonamides and 2-hydroxy-naphthalene-3,6- and -3,7-disulfonamides in which one hydrogen atom or both hydrogen atoms of the sulfonamide groups are substituted by ethyl, hydroxyethyl or diethylaminoethyl groups. These compounds couple to give reddish-tinged blue to violet azo dyes of only moderate light fastness.

Diazotype materials, predominantly for the production of negative copies, with water-insoluble diazoimino compounds are also known, wherein the light-sensitive layer is adjusted to have an alkaline reaction and wherein 2,3-dihydroxy-naphthalene-6-sulfanilide is used as the blue coupler (U.S. Pat. No. 4,055,425). If this process is used for the production of positive copies, it is complicated because of the additional adjustment of the layer to an acid pH range. Moreover, this material does not couple at an adequate rate during conventional development and in particular during pressurized gas development.

It is therefore the object of the invention to provide new compounds in which the disadvantages of the above-mentioned compounds are not present or are present only to a very much reduced extent and which are superior to the hitherto known compounds with respect to the light fastness of their azo dyes. The stated object is achieved by derivatives of 2-hydroxy-naphthalene, of the general formula wherein A is and X is —OH or and $R_1$, $R_2$, $R_3$, and $R_4$, are identical or different and are hydrogen, cycloalkyl having up to 8 carbon atoms, which is optionally substituted by lower alkyl groups, aralkyl having up to 10 carbon atoms or aryl which is substituted by lower alkyl, lower alkoxy, halogenalkyl or alkyl-substituted amino groups or by halogen, or $R_1$ and $R_2$ or $R_3$ and $R_4$ in each case are, conjointly with the nitrogen atom to which they are attached, identical or different heterocyclic groups which are optionally substituted by lower alkyl.

Particularly suitable are derivatives of 2-hydroxy-naphthalene, in which $R_1$, $R_2$, $R_3$, and $R_4$, are identical or different and are hydrogen, cycloalkyl having up to 7 carbon atoms, aralkyl having up to 10 carbon atoms or aryl having up to 10 carbon atoms, which is substituted by alkyl, alkoxy, halogenalkyl or dialkylamino groups having up to 4 carbon atoms or by halogen, or $R_1$ and $R_2$ or $R_3$ and $R_4$, are, conjointly with the nitrogen atom to which they are attached, pyrrolidine, piperidine, piperazine, morpholine, thiomorpholine or hexamethyleneimine.

Particularly suitable are those 2-hydroxy-naphthalene derivatives in which X is a hydroxyl group. Because of their increased coupling rate, compounds of this type are particularly suitable in combination with diazo compounds of lower coupling rate, such as are customarily used in two-component diazo materials. In this case, those derivatives are outstanding which carry a sulfonamide radical in which $R_1$ is hydrogen and $R_2$ is phenyl which is substituted by at least one lower alkyl, lower alkoxy, halogenalkyl or dialkylamino group and/or by halogen, preferably phenyl which is substituted by at least one methyl or trifluoromethyl group and/or by chlorine.

Those derivatives of 2-hydroxy-naphthalene also prove suitable in which X is a sulfonamide group. Because of their lower coupling rate, compounds of this type are particularly suitable in combination with diazo compounds of high coupling rate, such as are customarily used in single component diazotype materials. In these compounds, $R_1$ and $R_3$ are hydrogen, and $R_2$ and $R_4$ are identical or different and are phenyl which is substituted by at least one lower alkyl, lower alkoxy, halogenalkyl or dialkylamino group and/or by halogen, preferably phenyl which is substituted by at least one methyl or trifluoromethyl group and/or by chlorine.

The new compounds are employed with particular advantage in the diazotype process wherever sensitizing formulations based on a solvent are used. Those compounds of the general formula are preferred for use in aqueous formulations, in which $R_1$ and/or $R_3$ are hydrogen and $R_2$ and $R_4$ are identical or different cycloalkyl, aralkyl or aryl, which are substituted by salt-forming basic groups, for example the dialkylamino group. Particularly preferred are those compounds of the general formula in which $R_1$ and/or $R_3$ are hydrogen and $R_2$ and/or $R_4$ are phenyl which is substituted by at least one basic group which is present as such, as a salt, as a heavy metal complex salt or as a quaternary ammonium salt. The salt formation on the basic group can be effected in known manner with any acid which forms stable amine salts. The hydrochlorides are preferred. The zinc chloride complex salts are preferred as complex heavy metal/amine salts. If the basic group is quaternized, the fourth organic group preferably is a lower alkyl group. Optionally, the basic group also can be an alkyl-substituted heterocyclic radical. Preferred basic heterocyclic compounds are those having 5–8 ring members, such as pyrrolidine, piperidine, piperazine, morpholine, thiomorpholine or hexamethyleneimine.

Examples of the derivatives, according to the invention, of 2-hydroxy-naphthalene, which are preferentially used as coupling components in diazotype materials, are listed in the formulae below, together with their melting points or decomposition points.

The derivatives, according to the invention, of 2-hydroxynaphthalene can be prepared by the following method, described for the case of the 2,3-dihydroxy-naphthalene-6-sulfonamides:

2,3-Dihydroxy-naphthalene-6-sulfonic acid (Na salt), industrially known under the name "Dinol salt", is reacted according to the Schotten-Baumann reaction with benzene sulfonyl chloride at 60°–70° C. and at a pH of 7–8 to give 2,3-dibenzene sulfonyloxy-naphthalene-6-sulfonic acid (Na salt). After isolation and drying, this salt is converted with excess phosphorus oxychloride into the corresponding sulfochloride. The reaction mixture is stirred into ice water and 2,3-dibenzene sulfonyloxy-naphthalene-6-sulfochloride is isolated as a colorless crystalline substance (melting point: 151°–152° C.). By reacting the sulfochloride with the amine bases, substituted by the groups $R_1$ and $R_2$, in toluene at 100°–115° C., the corresponding 2,3-dibenzene sulfonyloxy-naphthalene-6-sulfonamides are obtained, initially in an oily form; by treatment with dilute hydrochloric acid, however, they then solidify very rapidly to colorless crystalline compounds. The benzene sulfonyl protective group is subsequently split-off by brief heating in an aqueous-alkaline solution at 80°–90° C. (steam bath temperature). By acidifying the alkaline solution, the 2,3-dihydroxy-naphthalene-6-sulfonamides are precipitated, initially in an oily form, but they become solid after a short time as a result of seeding or scratching on the inside wall of the vessel (Yield: 70–80% of theoretical, relative to Dinol salt).

The preparation of the 2-hydroxy-naphthalene-3,6- and -3,7-disulfonamides takes place in an analogous manner, except that 2-hydroxy-naphthalene-3,6- or -3,7-disulfonic acid (Na salt) respectively are employed as the starting material in the synthesis of these compounds. 2-Benzene sulfonyloxy-naphthalene-3,6-disulfochloride, obtained as an intermediate stage in this synthesis method, melts at 188°–190° C., and the isomeric 2-benzene sulfonyloxy-naphthalene-3,7-disulfochloride melts at 177°–181° C. By reacting the sulfochlorides with the amine bases substituted by the groups $R_1$ and $R_2$ or $R_3$ and $R_4$, the corresponding 3,6- or 3,7-disulfonamides are obtained which are converted, by splitting-off the benzene sulfonyl protective groups, into the 2-hydroxy-naphthalene-3,6- or 3,7-disulfonamides respectively (yields: 60–70% of theoretical, relative to starting material).

As a support for the diazotype layer, any conventional base is suitable, such as, for example, coated or uncoated, opaque, transparent or colored papers, textiles or plastic films. Particularly suitable plastic films are those composed of a cellulose ester, such as cellulose 2½-acetate or cellulose triacetate, of polypropylene, of polyester, such as polyethylene terephthalate, or of vinyl polymers, such as polyvinyl acetate or polystyrene.

The diazo compounds used together with the coupling components according to the invention for the production of blue color shades are known. Predominantly, these are derivatives of p-phenylenediamine diazotized on one side and having, on the amino group, at least one substituent, for example optionally substituted alkyl, cycloalkyl, aralkyl or aryl. Those diazo compounds of the type of p-phenylenediamine diazotized on one side are preferred which are substituted in the 2-position and 5-position relative to the diazonium group by an alkoxy group and in which the substituents on the amino nitrogen atom, to which they are attached, are linked to give a heterocyclic ring system, for example a morpholine ring.

The derivatives, according to the invention, of 2-hydroxynaphthalene couple with the diazo compounds known in the diazotype process, to give deep blue azo dyes. Compared with known blue azo dyes, the new dyes are distinguished by a light fastness which in many cases is considerably improved. The best results are obtained if the molar ratio of the diazo compound and the coupling component is between (1–1.2):1, preferably 1.1:1. Such a ratio is surprising inasmuch as customarily an excess of coupling component is employed. If, however, these customary ratios are employed, reduced light-fastness properties are obtained. Light-fastness properties depending upon the ratio of the diazo components, however, were hitherto not known.

Compared with the 2-hydroxy-3-naphthoic acid amides and the derivatives substituted in the 6-position by a bromine atom or a methoxy group, the markedly lower inherent color of the derivatives according to the invention and the improved image background in diazo copies, associated therewith, are advantageous.

A further advantage of the derivatives, according to the invention, of 2-hydroxy-naphthalene, in particular of the 2,3-dihydroxy-naphthalene-6-sulfonamides of the new type of compound, is their higher coupling rate, compared with that of the already known salts of 2,3-dihydroxy-naphthalene-6-sulfonic acid and the 2-hydroxy-3-naphthoic acid amide-6-sulfonamides. In combination with the diazo compounds, preferred in diazotype materials, of the type of p-phenylenediamine diazotized on one side, this higher coupling rate leads to a more rapid and more complete development. The advantage of the increased coupling rate is particularly of outstanding importance in applied technology, whenever the development of diazotype materials is to be carried out at low temperatures with dry ammonia gas under pressure or with moist ammonia gas in conventional duplicating apparatuses. The storage stability of the unexposed diazotype material is not adversely affected by the increased coupling rate. The derivatives, according to the invention, of 2-hydroxy-naphthalene can be employed, both singly and as a mixture with one another, as coupling components in diazotype materials. To obtain other desirable color shades, for example black, they also can be used as a mixture with components which upon coupling give other colors.

Accordingly, the present invention also relates to a diazotype material having at least one diazo compound in the lightsensitive layer, in which at least one 2-hydroxy-naphthalene of the general formula is contained as the coupling component.

The coupling components according to the invention, preferably used for two-component diazotype materials, are applied, together with the diazo components, to a suitable support in a known manner from an aqueous, aqueous-alcoholic or purely organic solution.

If plastic films are used as the support material, the diazotype constituents are preferably applied in the form of a lacquer solution to the layer support from an organic medium which contains a film-forming binder. The concentration of the dye-forming components in the binder can vary between 15 and 30 parts by weight per 100 parts by weight of binder. Examples of suitable binders are the most diverse polymeric substances, for example cellulose ethers, such as ethylcellulose, and cellulose esters, such as cellulose 2½-acetate, cellulose, triacetate, cellulose acetopropionate, cellulose acetobutyrate and cellulose butyrate; vinyl polymers, such as polyvinyl acetate, polyvinylidene chloride, vinyl chloride/vinyl acetate copolymers, poly-(methylmethacrylate) copolymers of alkyl acrylates and acrylic acid, and further polymers, for example polyphenylene oxide, polyolefins, such as polyethylene or polypropylene, and ethylene glycol/isophthalic acid/terephthalic acid terpolymers.

In addition to the dye-forming components, the light-sensitive layer additionally can contain acid stabilizers, such as hydrochloric acid, boric acid, citric acid, tartaric acid, formic acid and 5-sulfosalicylic acid. The adjuvants customary in the diazotype process also can be contained in the light-sensitive layer, for example inorganic salts, such as zinc chloride or ammonium sulfate for increasing the contrast, urea, dimethylurea, ethylglycol, ethylglycol monomethyl ether, glycerol, glycerol diacetate and glycerol triacetate as coupling accelerators, thiourea and thiourea derivatives as anti-yellowing agents, as well as dyes in low concentrations for coloring the fully exposed areas of the diazo copy.

The invention will be further illustrated by reference to the following specific examples: Explanations for the examples:

A. The base lacquer used for the preparation of the diazotype materials in Examples 1–5 and 7–8 contains 7.5 percent by weight of cellulose acetopropionate dissolved in a solvent mixture composed of acetone, methanol, n-butanol and glycol monomethyl ether.

B. The optical densities of the developed film samples prepared according to Examples 1–5 and 7–8 are measured using a MACBETH Quantalog densitometer TD 205.

For the density measurements in the visible range of the spectrum ($D_{vis.}$), the filter used is transparent in the region from 510–580 nm (Kodak, Wratten No. 93) and, for the density measurements in the ultraviolet range of the spectrum ($D_{uv}$), the filter used is effective in the region from 310–410 nm (Schott, UG 4).

C. To test and assess the light-fastness of the diazotype dyes, produced in full-tone development, of Examples 1, 7 and 8, a commercially available reader (Saul, LG 16F4) was used which was fitted with a halogen incandescent lamp of 15 V/150 W, a cooling unit and a lens system for 24-fold magnification.

D. The diazo film samples prepared according to Examples 1–5 and 7–8 were exposed and developed in a commercially available sheet microfilm-duplicating apparatus (Kalle, Ozafiche).

The diazotype material of Example 6 was exposed and developed in a commercially available diazo printing apparatus.

The diazo films of Example 5 were developed with dry ammonia gas under pressure in a commercially available aperture card-duplicating apparatus.

EXAMPLE 1

Starting from 50 ml of base lacquer in each case, 4 different coating solutions of the following composition were prepared.

90 mg: of 5-sulfosalicylic acid
90 mg: of zinc chloride
290 mg: of 2,5-dibutoxy-4-morpholinobenzenediazonium fluoborate
$0.69 \times 10^{-3}$ mole of blue coupler, the blue couplers used being:
1. 191 mg: of 2-hydroxy-3-naphthoic acid N-(2-methylphenyl)-amide (molecular weight: 277)
2. 110 mg: of 2,3-dihydroxy-naphthalene (molecular weight: 160)
3. 307 mg: of 2-hydroxy-3-naphthoic acid N-(2-methylphenyl)-amide-6-sulfonic acid N-(2-methylphenyl)-amide (molecular weight: 446)
4. 264 mg: of 2,3-dihydroxy-naphthalene-6-sulfonic acid N-(3-trifluoromethylphenyl)-amide (molecular weight: 383), formula 13.

Each of the solutions was applied to a 100 μm thick polyethylene terephthalate film, provided with an adhesion-promoting layer, in such a way that the various diazo film materials obtained after drying in a circulating air oven at 60°–70° C. could be developed to an optical visual density of 1.60–2.20. The diazo film materials prepared in this way are numbered consecutively from 1–4, corresponding to the sensitizing solutions used. To ensure complete development, the diazo film samples 1–4 were each developed twice. The following color shades resulted:

| Diazo film sample 1: | slightly reddish-tinged blue |
|---|---|
| Diazo film sample 2: | violet |
| Diazo film sample 3: | greenish-tinged blue |
| Diazo film sample 4: | reddish-tinged blue. |

Subsequently, the diazo films developed to the full tone were exposed for 12 hours to diffuse daylight.

A strip of 0.5 cm × 5 cm area was cut from each of the full tone samples thus treated and this strip was marked, on the side carrying the dye, by means of a circular measurement area of about 0.3 cm². The optical visual density ($D_{vis.}$) in the green region of the spectrum (Kodak, Wratten filter No. 93) was determined in each measurement area.

The marked film strips, developed to the full tone, were then simultaneously exposed to the spectral emission of the light source of a commercially available reader (Saul, LG 16F4). After an irradiation time of 4 hours in each case, the optical visual density ($D_{vis., END}$) was determined again in the measurement areas of the full tone samples and was compared with the initial density ($D_{vis., IN.}$). Altogether, the full tone samples were irradiated in the reader for 36 hours.

To assess the light stability of the diazo film samples 1–4, their optical visual densities at the beginning (IN.) and at the end (END) are compiled in Table 1. The "half-life" ($\tau$) of each full tone sample, i.e, the time after which the optical visual density has fallen to half its value measured at the beginning of the irradiation test, is also included in the table.

TABLE 1

| Sample | $D_{vis.}$ IN. | $D_{vis.}$ END | Residual Density (in %) | $\tau$ (in hours) |
|---|---|---|---|---|
| 1 | 2.06 | 0.05 | 2.5 | 5 |
| 2 | 2.24 | 0.20 | 9 | 11.5 |
| 3 | 1.62 | 0.34 | 21 | 18 |
| 4 | 1.77 | 0.90 | 50 | 36 |

A comparison of the density values very impressively shows the superior light stability of the full tone sample 4. While the azo dye of the full tone sample 4 still has 50% of its original optical density after standing in the reader for 36 hours, the optical densities of the azo dyes of the comparative samples 2 and 3 have already fallen to 9 and 21% respectively, and that of the comparative sample 1 has even fallen to 2.5% of its original optical density.

Comparing the half lives "$\tau$" of the full tone samples 1 to 4, the great superiority of the sample 4 according to the invention after standing in the reader for 36 hours also can be very clearly seen. The half-life of the full tone sample 4 is longer by factors of 7, 3, and 2, compared with the half lives of the full tone samples 1, 2, and 3, respectively.

Figure 1:
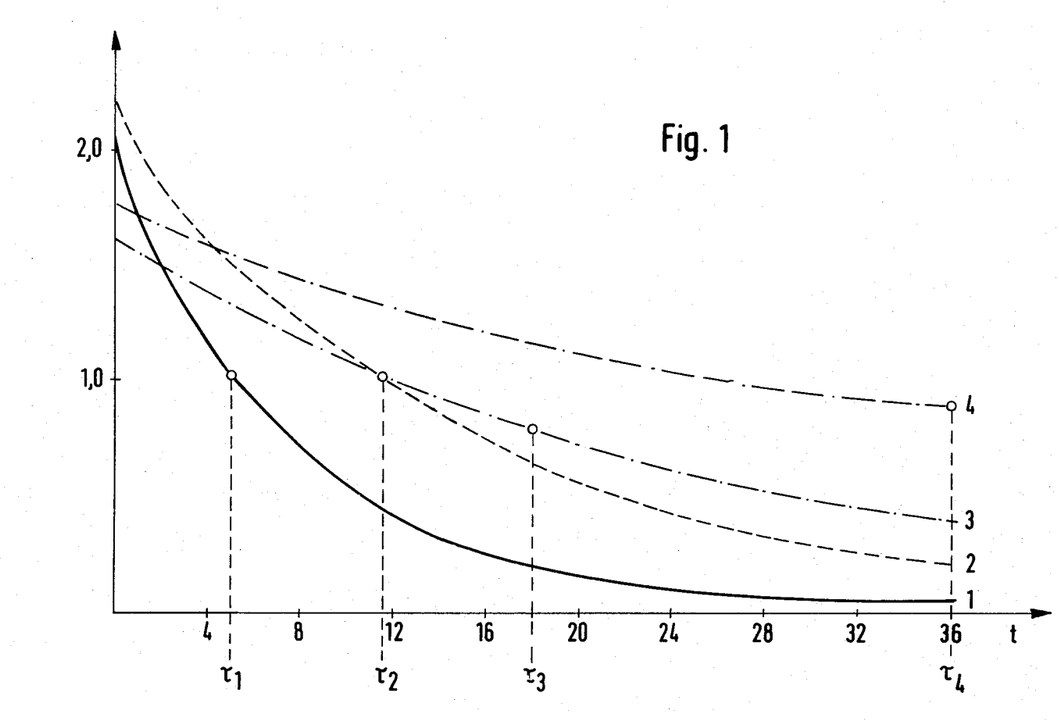

The measured optical densities (ordinate) and the half lives ($\tau$) of the full tone samples 1–4 are graphically plotted in FIG. 1 as a function of the irradiation time (t) in the reader used.

EXAMPLE 2

Starting from 50 ml of base lacquer in each case, 6 different coating solutions of the following composition were prepared:

90 mg: of 5-sulfosalicylic acid
90 mg: of zinc chloride
260 mg: of 2,5-dibutoxy-4-morpholinobenzenediazonium fluoborate
$0.69 \times 10^{-3}$ mole of blue coupler, the blue coupler used being:
5. 236 mg: of 2-hydroxy-3-naphthoic acid N-(3-morpholinopropyl)-amide (molecular weight: 344)
6. 191 mg: of 2-hydroxy-3-naphthoic acid N-(2-methylphenyl)-amide (molecular weight: 277)
7. 307 mg: of 2-hydroxy-3-naphthoic acid N-(2-methylphenyl)-amide-6-sulfonic acid N-(2-methylphenyl)-amide (molecular weight: 446)
8. 227 mg: of 2,3-dihydroxy-naphthalene-6-sulfonic acid N-(2-methylphenyl)-amide (molecular weight: 329), formula 8
9. 332 mg: of 2-hydroxy-naphthalene-3,6-disulfonic acid N-(2-methylphenyl)-amide (molecular weight: 482), formula 17
10. 332 mg: of 2-hydroxy-naphthalene-3,7-disulfonic acid N-(2-methylphenyl)-amide (molecular weight: 482), formula 18

A diazo film sample was prepared from each solution, as described in Example 1. Subsequently, a strip of each diazo film sample was developed to the full tone in each case. A further strip of each diazo film sample was fully and completely exposed and subsequently likewise developed. The optical densities of the developed film samples thus obtained were determined in the visible ($D_{vis.}$) and ultraviolet ($D_{uv}$) ranges of the spectrum. The measured density values are compiled in Table 2.

Upon development, the samples 5 and 7 gave greenish-tinged blue color shades, the samples 6, 9, and 10 gave neutral blue color shades and the sample 8 gave a reddish-tinged blue color shade.

TABLE 2

| Sample | Full Tone $D_{vis.}$ | $D_{uv}$ | Image Background $D_{vis.}$ | $D_{uv}$ |
|---|---|---|---|---|
| 5 | 1.44 | 0.69 | 0.06 | 0.28 |
| 6 | 2.08 | 0.75 | 0.05 | 0.20 |
| 7 | 1.49 | 0.73 | 0.05 | 0.17 |
| 8 | 1.65 | 0.44 | 0.04 | 0.07 |
| 9 | 1.44 | 0.58 | 0.04 | 0.11 |
| 10 | 1.44 | 0.58 | 0.04 | 0.12 |

The measured density values show that the UV densities of the image background of the film samples 8, 9, and 10, are markedly lower than those of the comparative samples 5, 6, and 7. The blue couplers according to the invention, used in the samples 8, 9, and 10, are therefore more suitable as shading components for the manufacture of materials for intermediate originals, than those of the samples 5, 6, and 7.

EXAMPLE 3

Starting from 50 ml of base lacquer in each case, 3 different solutions were prepared:
90 mg: of 5-sulfosalicyclic acid
90 mg: of zinc chloride
260 mg: of 2,5-dibutoxy-4-morpholino benzenediazonium fluoborate
$0.69 \times 10^{-3}$ mole of blue coupler.

The following blue couplers were used:
11. 287 mg: of 2-hydroxy-3-naphthoic acid N-(phenyl)-amide-6-sulfonic acid N-(phenyl)-amide (molecular weight: 418)
12. 214 mg: of 2,3-dihydroxy-naphthalene-6-sulfonic acid N-morpholide (molecular weight: 309), formula 2
13. 240 mg: of 2,3-dihydroxy-naphthalene-6-sulfonic acid N-(4-chlorophenyl)-amide (molecular weight: 350), formula 11.

As described in Example 1, a diazo film sample was prepared from each solution, numbered consecutively from 11-13 corresponding to the solutions used, and a strip of each film sample, of about 5 cm × 6 cm area, was developed once in the developer part of a commercially available sheet film duplicating apparatus.

Immediately after leaving the developer part, the UV density ($D_{UV, IN}$) of the full tone sample obtained was measured. The proportion of the diazo compound, which had not been coupled to give an azo dye, was photolytically destroyed by the measuring light and the UV density was thus lowered. The smaller the difference $D_{UV, IN} - D_{UV, END}$ ($\Delta D$), the faster the particular film material can be developed, i.e. the difference $\Delta D$ is a measure of the developing speed and is inversely proportional thereto.

To evaluate the developing speed of the film samples 11-13, the UV densities $D_{UV, IN}$ and $D_{UV, END}$ as well as the density differences $\Delta D$ are compiled in Table 3.

TABLE 3

| Sample | UV Densities $D_{UV, IN.}$ | $D_{UV, END}$ | $\Delta D$ |
|---|---|---|---|
| 11 | 0.98 | 0.64 | 0.34 |
| 12 | 0.54 | 0.53 | 0.01 |
| 13 | 0.42 | 0.39 | 0.03 |

Comparing the density differences $\Delta D$ of the samples 11-13, it is seen very clearly that, in the film samples 12 and 13, the dye coupling has proceeded virtually to completion, while the comparative sample 11, with a known blue coupler in the light-sensitive layer, contains a substantially greater amount of residual diazo compound. This means that the film samples 12 and 13 develop considerably faster than the comparative sample 11. The behavior of all the compounds, according to the invention, listed in the formulae below is similar in principle.

EXAMPLE 4

A polyethylene terephthalate film provided with an adhesion-promoting layer is coated on one side on the subbed surface with a solution of the following composition:
50 ml: of base lacquer
90 mg: of 5-sulfosalicyclic acid
90 mg: of zinc chloride
332 mg: of 2-hydroxy-naphthalene-3,6-disulfonic acid N-(2-methylphenyl)-amide, formula 17
250 mg: of 2,5-diethoxy-4-(4'-methylphenylmercapto)-benzenediazonium fluoborate.

After drying, the sensitized film is exposed under a transparent silver image original and is developed in a commercially available sheet film duplicating apparatus (KALLE, Ozafiche). A contrast-rich film copy of the original with reddish-tinged blue lines on a clear transparent background is obtained.

The unexposed diazo film material has good storage stability.

EXAMPLE 5

Starting from 50 ml of base lacquer in each case, two different coating solutions of the following composition were prepared:
90 mg: of 5-sulfosalicyclic acid
90 mg: of zinc chloride
290 mg: of 2,5-dibutoxy-4-morpholino-benzenediazonium fluoborate
$0.69 \times 10^{-3}$ mole of blue coupler, the blue couplers used being:
14. 264 mg: of 2,3-dihydroxy-naphthalene-6-sulfonic acid N-(3-trifluoromethylphenyl)-amide, formula 13
15. 230 mg: of 2,3-dihydroxy-naphthalene-6-sulfonic acid (aniline salt).

As described in Example 1, a diazo film sample with the consecutive numbering 14-15 was prepared from each solution. Two small part pieces of about 3 cm × 5 cm area in each case were then cut off from each of these two film samples. The cut-offs were designated respectively as 14a and 14b, and 15a and 15b. 14a and 15a were developed with moist ammonia gas at about 60°-70° C., and 14b and 15b were developed under pressure with dry ammonia gas at about 20°-25° C. The optical visible densities and color shades, obtained under the differing development conditions, are compiled in Table 4.

TABLE 4

| Sample | NH₃ gas, moist 60–70° C. | | NH₃ gas, dry (pressure) 20–25° C. | |
|---|---|---|---|---|
| | $D_{vis.}$ | Color Shade | $D_{vis.}$ | Color Shade |
| 14a | 1.60 | reddish-tinged blue | — | — |
| 14b | — | — | 1.45 | neutral blue |
| 15a | 1.17 | neutral blue | — | — |
| 15b | — | — | 0.58 | greenish-tinged gray |

The development results show that, under differing development conditions, the film sample 15 develops to give markedly differing optical visible densities and color shades. By contrast, the film sample 14 with the compounds according to the invention displays these differences to a markedly smaller extent.

EXAMPLE 6

The following solution was applied to a blue-colored, naturally transparent paper lacquered with cellulose acetate (about 50–54% of acetic acid) (lacquer application of 10–20 g/m²), the excess was removed in a suitable manner and the material was dried:
32.5 ml: of isopropanol
12.5 ml: of water
2.5 ml: of formic acid
1.25 g: of citric acid
0.75 g: of boric acid
1.5 g: of thiourea
1.55 g: of 2,3-dihydroxy-naphthalene-6-sulfonic acid N-(4-diethylaminophenyl)-amide, Formula 16
1.53 g: of 2,5-diethoxy-4-morpholino-benzenediazonium chloride (zinc chloride double salt)

After exposure under an original, development with moist ammonia gas gave very contrast-rich, reddish-tinged blue lines, coupled with very good transparency of the background of the copy.

EXAMPLE 7

A polyethylene terephthalate film, provided on both sides with an adhesion-promoting layer, was coated on one side with a solution of
1.0 g of Fettgelb 5G (C.I. Solvent Yellow 68) in
100 ml of base lacquer.

The film was dried at 60°–70° C. in a circulating air oven, and a composite of support film and yellow coating was obtained. The dry layer weight was about 6 g/m².

After drying, the other side of the film was sensitized with a solution of the following composition:
120 ml: of base lacquer
240 mg: of 5-sulfosalicylic acid
400 mg: of N,N-dimethylurea
540 mg: of 2,3-dihydroxynaphthalene-6-sulfonic acid N-(4-chlorophenyl)-amide, Formula 11
660 mg: of 2,5-dibutoxy-4-morpholino-benzenediazonium fluoborate.

After drying again in a circulating air oven at 60°–70° C., the sensitized film prepared in this way was exposed under a transparent silver image original and developed. A very contrast-rich two-colored copy of the original with a blue azo dye image on one side of the film and a yellow image background on the other side of the film was obtained. A greenish-tinged black color image on a yellow background was seen through a film projector or in a microfilm reader. The legibility of the film copy was very good. If, in place of the blue coupler according to the invention, the equivalent amount of the known blue coupler 2-hydroxy-3-naphthoic acid N-(2-methylphenyl)-amide is used in the light-sensitive layer, a two-color film copy is likewise obtained after imagewise exposure. On viewing in the film projector or in a microfilm reader, a greenish-tinged blue color image on a yellow background is seen, but its contrast and legibility are inferior to that obtained when using the blue coupler according to the invention.

It is not possible to produce a further copy an diazo material from either of the two diazo film copies.

Comparing the light stabilities of the two film copies, it is seen that, after 12 hours' standing, the film copy with the blue coupler according to the invention fades considerably less and, for that reason, is still substantially more legible than the comparative copy.

To evaluate the better light stability, a film sample (Sample 17), which contains the blue coupler according to the invention, and a film sample (Sample 18), which contains the blue coupler used for comparison purposes, were developed to the full tone. One cut-off from each of these two full tone samples was then simultaneously exposed in a microfilm reader to the spectral emission of the light sources for 12 hours. The optical density values at the beginning and at the end of the irradiation time are complied in Table 5 which follows.

TABLE 5

| Sample | $D_{vis.}$ IN. | $D_{vis.}$ END | Residual density (in %) | τ (in hours) |
|---|---|---|---|---|
| 17 | 1.60 | 0.80 | 50 | 12 |
| 18 | 1.51 | 0.24 | 16 | 4 |

Comparing the half lives of the full tone samples 17 and 18, it is seen that the density of the full tone sample 17 has fallen to half its original value after only 12 hours' standing in the reader, while the density of the comparative sample 18 has already fallen to half its original value after 4 hours. Therefore, the light stability of the full tone sample 17 on the reader is greater by a factor of 3 than that of the comparative sample 18.

EXAMPLE 8

A polyethylene terephthalate film, provided with an adhesion-promoting layer, was coated on one side on the subbed surface with a solution of the following composition:
100 ml: of base lacquer
410 mg: of 5-sulfosalicyclic acid
168 mg: of 2-methyl-resorcinol
33 mg: of 2,2',4,4'-tetrahydroxy-diphenyl sulfide
200 mg: of glycerol triacetate
168 mg: of zinc chloride
60 mg: of N,N-dimethylurea
320 mg: of 2,3-dihydroxynaphthalene-6-sulfonic acid N-(4-chlorophenyl)-amide, formula 11
726 mg: of 2,5-dibutoxy-4-morpholino-benzenediazonium fluoborate
77 mg: of 4-dipropylamino-benzenediazonium fluoborate.

After drying, the coated film was exposed under a transparent silver image original and was developed. A very contrast-rich film copy of the original with black lines on a clear transparent background was obtained. In commercially available microfilm readers, the film copy shows an excellent light stability.

If, in place of the blue coupler of formula 11, according to the invention, an equivalent amount of 6- methoxy-2-hydroxy-3-naphthoic acid N-(3-morpholino-propyl)-amide according to German patent application No. P 27 46 551.6 is used in the light-sensitive layer, a copy with black lines on a slightly yellow-colored transparent background is likewise obtained. The light stability of this copy in the microfilm reader, however, is markedly lower than that of the film copy prepared with the compound according to the invention.

To demonstrate the better light stability of the film image dyes in the reader, compared with known diazo films giving black duplicates, a film sample (Sample 19), which contains the blue coupler of formula 11, according to the invention, and a film sample (Sample 20), which contains the blue coupler for comparison purposes, were developed to the full tone. Cut-offs of these two full tone samples were than simultaneously irradiated in a reader for 12 hours. The optical density values of the full tone samples 19 and 20 at the beginning and at the end of the irradiation period are compiled in Table 6 which follows.

TABLE 6

| Sample | $D_{vis.}$ IN. | $D_{vis.}$ END | Residual density (in %) | τ (in hours) |
|---|---|---|---|---|
| 19 | 1.56 | 1.25 | 80 | 30 |

TABLE 6-continued

| Sample | $D_{vis.}$ IN. | $D_{vis.}$ END | Residual density (in %) | τ (in hours) |
|---|---|---|---|---|
| 20 | 1.55 | 0.28 | 18 | 6 |

Comparing the residual densities of the full tone samples 19 and 20, it is seen that the full tone sample 19 still has 80% of its original optical density after 12 hours' standing in the reader, while the full tone sample 20 after the same period has only 18% of its original optical density. Therefore, the light stability of the full tone sample 19 after 12 hours' standing in the reader is greater by a factor of 4.5 than that of the comparative sample 20.

with $A = -SO_2-N\begin{matrix}R_1\\R_2\end{matrix}$ and $X = -OH$ or $-SO_2-N\begin{matrix}R_3\\R_4\end{matrix}$

| No. | X | A (in position) | $R_1$ | $R_2$ | Melting Point (°C.) |
|---|---|---|---|---|---|
| 1 | HO | 6 | H | cyclohexyl-CH₃ | 68–70 |
| 2 | HO | 6 | | morpholino (N-H, O) | 218–220 |
| 3 | HO | 6 | | N-methylpiperazinium · benzenesulfonate (⊕/⊖SO₃) | > 200° (decomposition) |
| 4 | HO | 6 | H | –(CH₂)₂–phenyl | 77–80 |
| 5 | HO | 6 | H | m-chlorophenyl | 168–170 |
| 6 | HO | 6 | H | p-methylphenyl | 50–55 |
| 7 | HO | 6 | H | p-methylphenyl | 178–179 |

-continued

| No. | X | A (in position) | $R_1$ | $R_2$ | Melting Point (°C.) |
|---|---|---|---|---|---|
| 8 | HO | 6 | H |  | 204–205 |
| 9 | HO | 6 | H |  | 216–218 |
| 10 | HO | 6 | H |  | 192–193 |
| 11 | HO | 6 | H |  | 197–198 |
| 12 | HO | 6 | H |  | 188–190 |
| 13 | HO | 6 | H |  | 201–202 |
| 14 | HO | 6 | H |  | 177–180 |
| 15 | HO | 6 | H |  | 186–188 |
| 16 | HO | 6 | H |  | 191–195 |
| 17+ |  | 6 | H |  | 166–167 |
| 18+ |  | 7 | H |  | 229–230 |

-continued

| No. | X | A (in position) | R₁ | R₂ | Melting Point (°C.) |
|---|---|---|---|---|---|
| 19 | HO | 6 | H |  | 268–270 |
| | †R₃ = H<br>R₄ =  | | | | |

It will be obvious to those skilled in the art that many modifications may be made within the scope of the present invention without departing from the spirit thereof, and the invention includes all such modifications.

What is claimed is:

1. A diazotype material having at least one diazo compound in a light-sensitive acid stabilized layer, which comprises, as a coupling component, at least one 2-hydroxy-naphthalene of the general formula wherein A in the 6- or 7-position is $$-SO_2-N\begin{matrix}R_1\\R_2\end{matrix}$$

R₁ is hydrogen,
R₂ is an aryl group substituted by halogen alkyl or halogen, or
R₁ and R₂ are, conjointly with the nitrogen atom to which they are attached, pyrrolidine, piperidine, piperazine, morpholine, thiomorpholine, or hexamethyleneimine.

2. A diazotype material according to claim 1 in which the molar ratio of diazo compound to the coupling component is in the range of about (1–1.2):1.

3. A diazotype material as claimed in claim 1 wherein R₂ is phenyl substituted by at least one trifluoromethyl group and/or by chlorine.

* * * * *